United States Patent [19]

Wang et al.

[11] 4,321,267
[45] Mar. 23, 1982

[54] **1-SUBSTITUTED-4 (1H)-PYRIDINONE HYDRAZONES ACTIVE AGAINST *GIARDIA LAMBLIA* AND *TRICHOMONAS VAGINALIS***

[75] Inventors: Ching C. Wang, Watchung; Michael H. Fisher, Ringoes, both of N.J.

[73] Assignee: Merck & Co., Inc., Rahway, N.J.

[21] Appl. No.: 194,713

[22] Filed: Oct. 6, 1980

[51] Int. Cl.$^3$ .............................................. A61K 31/44
[52] U.S. Cl. .................................................... 424/263
[58] Field of Search ........................................ 424/263

[56] References Cited

U.S. PATENT DOCUMENTS 4,083,984  4/1978  Fisher et al. ........................ 424/263

OTHER PUBLICATIONS

Douglas et al., *Journal of Medicinal Chemistry*, vol. 20, pp. 939–943 (1977).
Altman, L. K., *The New York Times*, Jun. 10, 1980, p. C-1.
Dykers, *Medical Intelligence*, vol. 293, pp. 23–24 (1975).
Kerlin et al., *Digestive Diseases*, vol. 23, pp. 940–942 (1978).
Hartong et al., *Gastroenterology*, vol. 77, pp. 61–69 (1979).
Craun, *The American Journal of Public Health*, vol. 69, pp. 817–819 (1979).
Fouts et al., *The Journal of Infectious Diseases*, vol. 141, pp. 137–143 (1980).
Wisdom et al., *The British Journal of Venereal Diseases*, vol. 41, pp. 90–96 (1965).
Naguib et al., *The Journal of Obstetrics and Gynecology*, vol. 27, pp. 607–616 (1966).
Hughes et al., *Journal of Obstetrics and Gynecology of the British Commonwealth*, vol. 73, pp. 821–827 (1966).
Ings et al., *Biochemical Pharmacology*, vol. 23, pp. 1421–1429 (1974).
Collection of Monographs from International Conference on the Chemistry, Pharmacology, & Clinical Application of Nitroimidazoles, Aug. 1980, pp. 33–36, 53–54, 61–62 and 67.

*Primary Examiner*—Allen J. Robinson
*Attorney, Agent, or Firm*—David L. Rose; Harry E. Westlake

[57] ABSTRACT

1-Substituted-4(1H)-pyridinone hydrazones, known as effective anti-coccidial agents, are useful as potent anti-giardiasis and anti-trichomoniasis agents.

6 Claims, No Drawings

1-SUBSTITUTED-4 (1H)-PYRIDINONE HYDRAZONES ACTIVE AGAINST *GIARDIA LAMBLIA* AND *TRICHOMONAS VAGINALIS*

BACKGROUND OF THE INVENTION

*Giardia lamblia*, a parasite that until recently was widely believed to be relatively harmless, now heads the list of the most common intestinal parasitic infections in the United States and some other countries. The parasite causes a diarrheal disease called giardiasis.

This infection causes a variety of intestinal symptoms, such as prolonged diarrhea, abdominal cramps, stomach pain, severe weight loss, fatigue, nausea and flatulence. Giardiasis can also cause malabsorption of nutrients and even retarded growth. Furthermore, giardiasis can mimic the symptoms of other conditions such as ulcers and gall bladder attacks. If misdiagnosed, a patient may have a series of costly, needless tests, and even surgery.

The infection can be successfully treated with one of three drugs: Atabrine, Flagyl or furazolidone. However, each of these drugs is known to cause adverse side effects. Until the present invention, no prophylactic drug has been found which can successfully protect against giardiasis. (L. K. Altman, M.D., *The New York Times*, June 10, 1980).

Trichomonas is an infection of the lower genitourinary tract, which may be induced in men and women by the protozoan parasite *Trichomonas vaginalis*. The infection may produce a few symptoms of such extreme discomfort and morbidity that intervention from a gynecologist or a urologist is necessary. The disease is of cosmopolitan distribution and apparently 10-25% of sexually mature females and 25-80% of their consorts are involved (E. A. Steck, The Chemotherapy of Protozoa Diseases, Vol. II, Section 3, 17-1 1971). Trichomoniasis is presently treated with flagyl(metronidazole).

The present invention relates to the use of a group of 1-substituted phenyl-4(1H)-pyridinone hydrazones which are more active and less toxic than Flagyl(metronidazole) and other commonly used drugs in the treatment of giardiasis and trichomoniasis in humans.

The 1-substituted-phenyl-4(1H)-pyridinone hydrazones and methods of preparation thereof have been disclosed in U.S. Pat. No. 4,083,984, issued Apr. 11, 1978. The utility disclosed therein is the control of coccidiosis in poultry such as chickens and turkeys. The protozoa responsible for coccidiosis are of the genus Eimeria.

SUMMARY OF THE INVENTION

The present invention is directed to the novel method for control and treatment of giardiasis, a parasitic infection in humans caused by a protozoan of the genus Giardia. As reported in the *New York Times* article, cited above, there is no drug which can adequately protect against giardiasis.

The novel compositions used in the present method can also be used for the prevention, treatment and control of trichomoniasis in men and women. Successful therapy of trichomoniasis with Flagyl (metronidazole) has been reported, however, the drug is mutagenic in bacteria and has been shown to be carcinogenic in animals.

Therefore, it is an object of the present invention to (1) provide for novel compositions comprising a 1-substituted-phenyl-4(1H)-pyridinone hydrazone with antigiardiasis and anti-trichomoniasis activities; and (2) provide a novel method for the prevention, control and/or treatment of giardiasis and trichomoniasis in humans through the administration of these novel compositions.

DETAILED DESCRIPTION OF THE INVENTION

The 1-substituted-4-(1H)-pyridinone hydrazones to be used in the methods and compositions of the present invention have the structural formula (I):

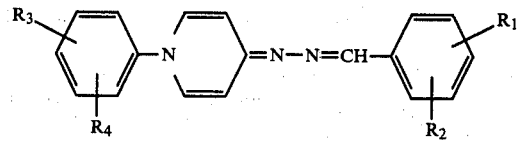

or a pharmaceutically acceptable salt thereof, wherein $R_1$ and $R_3$ are each separately selected from halogen, haloalkyl, alkylthio and cyano wherein the alkyl group contains 1 to 3 carbon atoms; and $R_2$ and $R_4$ are each separately selected from hydrogen and halogen.

As used in this specification, the prefix "lower" is meant to include groups having from 1 to 3 carbon atoms, i.e., methyl, ethyl and propyl including the isomers of propyl. Also, in this specification the term, "halo" is intended to include fluoro, chloro, bromo and iodo.

Although the substituents $R_1$ and $R_3$ may be positioned anywhere on the phenyl rings, a preferred group of 1-substituted-phenyl-4(1H)-pyridinone hydrazones are those wherein $R_1$ and $R_3$ are at the para positions and $R_1$, $R_2$, $R_3$ and $R_4$ are as defined above in formula (I).

A more preferred group of the compounds are those wherein $R_3$ is para to the pyridinone ring; $R_4$ is hydrogen; $R_1$ and $R_2$ are each separately selected from halogen, haloalkyl, alkylthio and cyano; and $R_2$ is hydrogen or halogen.

A still more preferred group of the compounds are those wherein $R_1$ and $R_2$ are as previously defined; $R_3$ is halogen especially chlorine and is para to the pyridinone ring; and $R_4$ is hydrogen.

An even more preferred group of the compounds are those wherein $R_1$ is fluorine, chlorine, bromine, trifluoromethyl, methylthio or cyano; $R_2$ is hydrogen, chlorine or bromine; $R_3$ is chlorine and para to the pyridinone ring; and $R_4$ is hydrogen.

Specifically, the most preferred compounds of the present invention are those designated:

(1) 1-[(4-chlorophenyl)-4(1H)-pyridinone]-2-[(4-chlorophenyl)methylene]hydrazone;

(2) 1-[(4-chlorophenyl)-4(1H)-pyridinone]-2-[(4-cyanophenyl)methylene]hydrazone;

(3) 1-[(4-chlorophenyl)-4(1H)-pyridinone]-2-[(4-methylthiophenyl)methylene]hydrazone;

(4) 1-[(4-chlorophenyl)-4(1H)-pyridinone]-2-[(3,4-dichlorophenyl)methylene]hydrazone;

(5) 1-[(4-chlorophenyl)-4(1H)-pyridinone]-2-[(4-trifluoromethylphenyl)methylene]hydrazone;

(6) 1-[(4-chlorophenyl)-4(1H)-pyridinone]-2-[(4-bromophenyl)methylene]hydrazone;

(7) 1-[(4-chlorophenyl)-4(1H)-pyridinone]-2-[2,4-dichlorophenyl)methylene]hydrazone; and (8) 1-[(4-chlorophenyl)-4(1H)-pyridinone]-2-[(4-fluorophenyl)methylene]hydrazone.

The above 1-substituted-4(1H)-pyridinone hydrazones and the method of preparation thereof are disclosed in U.S. Pat. No. 4,083,984, and are herein incorporated by reference.

The pharmaceutically acceptable salts of the above compounds are, for example, hydrohalides such as hydrochloride, hydrobromide; nitrate; fluorosulfate; sulfate or methosulfate; phosphate; or salts resulting from the neutralization of the base with an organic acid such as maleic, fumaric, tartaric, citric acetic, salicylic, succinic, benzoic, benzenesulfonic, glutamic or lactic acid. Such salts are equally active anti-giardiasis or anti-trichloromoniasis agents.

The activity of these compounds against *Giardia lamblia* and *Trichomonas vaginalis* are shown by the following test:

About 1.0–2.0 ml of a nutrient medium, for example, the modified Diamond's (TPS) medium at pH 7.05, together with about 10% by volume of heat-inactivated serum and about 1% by volume of an antibiotic-antimycotic mixture, is placed in each well of a multi-well plate. To this mixture, an aliquot of a suspension of *G. lamblia* cells containing about $10^6$ organism is added. Subsequently, each well is inoculated with a known concentration of one of the pyridinone hydrazones, for example, 1-[(4-chlorophenyl)-4(1H)-pyridinone]-2-[(4-chlorophenyl)methylene]-hydrazone. The multiwell plate containing the individual culture samples is incubated under anaerobic conditions at about 37° C. for about 16–24 hours. The number of viable cells remaining in each well are then counted, such as with a hemocytometer. The percentage of survival is determined by comparison to controls incubated with DMSO (dimethylsulfoxide) and the effective concentration (in parts per million) for 50% inhibition of growth ($ED_{50}$) is determined. It is established that the lower the $ED_{50}$ the higher the activity of the 1-substituted-4-(1H)-pyridinone hydrazone tested. The $ED_{50}$ values of a group of selected compounds are summarized below in Table I.

TABLE I

In vitro Anti-*G. lamblia* and Anti-*T. vaginalis* Activities of 1-Substituted-4(1H)-pyridinone hydrazones

| Active Compound | Anti-*G. lamblia* $ED_{50}$ (ppm) | Anti-*T. vaginalis* $ED_{50}$ (ppm) |
| --- | --- | --- |
| (1) 1-[(4-chlorophenyl)-4(1H)-pyridinone]-2-[(4-chlorophenyl)methylene]hydrazone | 1.45 | 2.63 |
| (2) 1-[(4-chlorophenyl)-4(1H)-pyridinone]-2-[(4-cyanophenyl)methylene]-hydrazone | 2.25 | 3.30 |
| (3) 1-[(4-chlorophenyl)-4(1H)-pyridinone]-2-[(4-methylthiophenyl)methylene]hydrazone | 1.10 | 2.88 |
| (4) 1-[(4-chlorophenyl)-4(1H)-pyridinone]-2-[(3,4-dichlorophenyl)methylene]hydrazone | 1.50 | 3.00 |
| (5) 1-[(4-chlorophenyl)-4(1H)-pyridinone]-2-[(4-trifluoromethylphenyl)methylene]hydrazone | 1.42 | 3.25 |
| (6) 1-[(4-chlorophenyl)-4(1H)-pyridinone]-2-[(4-bromophenyl)methylene]hydrazone | 1.25 | 3.63 |
| (7) 1-[(4-chlorophenyl)-4(1H)-pyridinone]-2-[(2,4-dichlorophenyl)methylene]hydrazone | 1.20 | 1.75 |
| (8) 1-[(4-chlorophenyl)-4(1H)-pyridinone]-2-[(4-fluorophenyl)methylene]hydrazone | 2.25 | 4.00 |
| metronidazole | 6.20 | <1.00 |

As indicated by Table I, a 4 to 6-fold improvement of anti-*G. lamblia* activity over metronidazole is achieved by the pyridinone hydrazones. The results from Table I also indicate that the compounds are potent anti-*T. vaginalis* agents.

The present method comprises the administration of an active compound, for example, 1-[(4-chlorophenyl)-4(1H)-pyridinone]-2-[(4-methylthiophenyl)methylene]-hydrazone, as an anti-giardiasis or anti-trichlomoniasis agent to a human patient in amounts ranging from about 0.05 to about 50 mg. per kg. of body weight, preferably from about 0.25 to about 25 mg. per kg. of body weight in a single dose or in 2 to 4 divided doses.

These compounds in the described dosages are usually administered orally. They may also be administered to individuals by injection. The oral pharmaceutical compositions of this invention usually consist of an active compound and some appropriate excipients and used in the form of tablets, troches, capsules, elixirs, suspensions, syrups, wafers, chewing gums and the like. The amount of an active compound in such a therapeutically useful composition or preparation usually ranges from about 2.5 mg. to about 2.5 g, preferably from about 5 mg. to about 500 mg. per unit dosage.

The previously described tablets, troches, capsules, pills and the like usually contain one or more of the following inactive ingredients: a binder such as gum tragacanth, acacia, corn starch or gelatin; an excipient such as dicalcium phosphate; a disintegrating agent such as corn starch, potato starch, alginic acid and the like; a lubricant such as megnesium stearate; and a sweetening agent such as sucrose, lactose or saccharin and/or a flavoring agent such as peppermint, oil of wintergreen, or cherry flavoring. When the dosage unit form is a capsule, it may contain in addition to materials of the above type, a liquid carrier such as fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially nontoxic in the amounts employed.

EXAMPLE 1

In each well of a multiwell plate is placed 1.4 ml of Diamond's TPS medium (See Table II) at pH 7.05, 10% by volume of heat-inactivated fetal bovine serum, and 1% by volume of an antibiotic-antimycotic solution (see Table III). A suspension of *Giardia lamblia* is centrifuged at 2,500 xg for 6 minutes. The pelleted cells are resuspended in a small volume of Diamond's medium, the cells are counted and each well inoculated with approximately $10^6$ organisms. A stock solution of 1-[(4-chlorophenyl)-4(1H)-pyridinone]-2-[(4-methylthiophenyl)-methylene]hydrazone in dimethylsulfoxide is made at a concentration of 150 $\mu$g/ml. The wells are then inoculated with various concentrations of the drug. The plates are incubated for 24 hours at 37° C. in an anaerobic Gas Pak jar. After 24 hours of incubation, each well is mixed and counted for viable organisms using a hemacytometer. The percentage of survival is determined by comparing the treated wells to controls treated with dimethylsulfoxide. Following the above procedure, 1-[(4-chlorophenyl)-4(1H)-pyridinone]-2-

[(4-methylthiophenyl)methylene]hydrazone is found to have an ED$_{50}$ of 1.10 ppm against *Giardia lamblia*.

TABLE I

| Composition of Diamond's TPS Medium | |
|---|---|
| Ingredients | Amounts |
| Trypticase (BBL) | 1.00 g. |
| Panmede, liver digest P & B | 2.00 g. |
| Glucose | 0.50 g. |
| L-cysteine monohydrochloride | 0.10 g. |
| Ascorbic acid | 0.02 g. |
| Sodium chloride | 0.50 g. |
| Potassium phosphate. monobasic | 0.06 g. |
| Potassium phosphate dibasic, anhydrous | 0.10 g. |
| Water, glass distilled | 87.50 ml. |
| pH adjusted to 7.0 with 1N NaOH | |

TABLE II

| Antibiotic Antimycotic Solution (100 ×) | |
|---|---|
| Ingredients | Amounts |
| Penicillin | 10,000 units |
| Streptomycin | 10,000 mcg |
| Fungizone ® | 25 mcg |
| Prepared in normal saline | |

Employing essentially the same procedure as described above, but substituting for 1-[(4-chlorophenyl)-4(1H)-pyridinone]-2-[(4-methylthiophenyl)methylene]-hydrazone used therein, other active compounds, there are obtained similar results indicating that each of the active compounds is active against *G. lamblia* as summarized above in Table I.

Similarly, following essentially the same procedure as described above, the hydrochloride salts of compounds (1) to (8) are found to be as equally active as the corresponding free bases.

EXAMPLE 2

Employing the method of Example 1, centrifuged cells of *T. vaginalis* 30001 are incubated with 1-[(4-chlorophenyl)-4(1H)-pyridinone]-2-[(4-methylthiophenyl)methylene]hydrazone at 37° C. for 24 hours. The results indicate that 1-[(4-chlorophenyl)-4(1H)-pyridinone]-2-[(4-methylthiophenyl)methylene]hydrazone is also an effective anti-*T. vaginalis* agent with an ED$_{50}$ value of 2.88 ppm.

Similarly, compounds (1), (2), and (4) to (8) and their corresponding pharmaceutically acceptable salts are also found to be active against *T. vaginalis*.

EXAMPLE 3

| Ingredient | Milligrams per Capsule |
|---|---|
| 1-[(4-chlorophenyl)-4(1H)-pyridinone]-2-[(3,4)-dichlorophenyl)methylene]-hydrazone | 10 |
| Starch | 100 |
| Magnesium stearate | 10 |
| Total weight | 120 mg. |

The active ingredient, starch and magnesium stearate are blended together. The mixture is used to fill hard shell gelatine capsules of a suitable size at a fill weight of 120 mg per capsule.

EXAMPLE 4

Preparation of Tablet Formulation

| Ingredient | Milligrams per Tablet |
|---|---|
| 1-[(4-chlorophenyl)-4(1H)-pyridinone]-2-[(4-trifluoromethylphenyl)methyle]-hydrazone | 12 |
| Lactose | 200 |
| Corn starch (for mix) | 50 |
| Magnesium stearate | 6 |

The active ingredient, lactose and corn starch (form mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compression into tablets in a suitable tableting machine. Each tablet contains 12 milligrams of the active ingredient.

What is claimed is:

1. A method for treating giardiasis and trichomoniasis in humans which comprises the administration to a person in a need of such therapy an amount effective for the treatment of giardiasis and trichomoniasis of a 1-substituted-4(1H)-pyridinone hydrazone of the formula:

$$R_3 \text{---} \underset{R_4}{\text{C}_6\text{H}_3} \text{---} N \text{---} \underset{}{\text{C}_5\text{H}_3\text{N}} = N-N=CH \text{---} \underset{R_2}{\text{C}_6\text{H}_3} \text{---} R_1$$

or a pharmaceutically acceptable salt thereof, wherein:
  (a) R$_1$ and R$_3$ are independently halogen, haloalkyl of from 1 to 3 carbon atoms, alkylthio of from 1 to 3 carbon atoms, or cyano; and
  (b) R$_2$ and R$_4$ are independently hydrogen or halogen.

2. The method of claim 1 wherein:
  (a) R$_1$ and R$_3$ are at the para positions and are independently halogen, haloalkyl of from 1 to 3 carbon atoms, alkylthio of from 1 to 3 carbon atoms, or cyano;
  (b) R$_2$ is hydrogen or halogen; and
  (c) R$_4$ is hydrogen.

3. The method of claim 2 wherein:
  (a) R$_1$ is halogen, haloalkyl of from 1 to 3 carbon atoms, alkylthio of from 1 to 3 carbon atoms or cyano;
  (b) R$_2$ is hydrogen or halogen;
  (c) R$_3$ is chlorine; and
  (d) R$_4$ is hydrogen.

4. The method of claim 2 wherein:
  (a) R$_1$ is fluorine, chlorine, bromine, trifluoromethyl, methylthio or cyano;
  (b) R$_2$ is hydrogen, chlorine or bromine;
  (c) R$_3$ is chlorine; and
  (d) R$_4$ is hydrogen.

5. The method of claim 2 wherein the 1-substituted-4-(1H)-pyridinone hydrazone is selected from the group consisting of:

(a) 1-[(4-chlorophenyl)-4(1H)-pyridinone]-2-[(4-chlorophenyl)methylene]hydrazone;
(b) 1-[(4-chlorophenyl)-4(1H)-pyridinone]-2-[(4-cyanophenyl)methylene]hydrazone;
(c) 1-[(4-chlorophenyl)-4(1H)-pyridinone]-2-[(4-methylthiophenyl)methylene]hydrazone;
(d) 1-[(4-chlorophenyl)-4(1H)-pyridinone]-2-[(3,4-dichlorophenyl)methylene]hydrazone;
(e) 1-[(4-chlorophenyl)-4(1H)-pyridinone]-2-[(4-trifluoromethylphenyl)methylene]hydrazone;
(f) 1-[(4-chlorophenyl)-4(1H)-pyridinone]-2-[(4-bromophenyl)methylene]hydrazone;
(g) 1-[(4-chlorophenyl)-4(1H)-pyridinone]-2-[(2,4-dichlorophenyl)methylene]hydrazone; and
(h) 1-[(4-chlorophenyl)-4(1H)-pyridinone]-2-[(4-fluorophenyl)methylene]hydrazone.

6. The method of claim 1 wherein the 1-substituted-4(1H)-pyridinone hydrazone is administered to a patient in need of such therapy orally.

* * * * *